(12) United States Patent
Kriegler et al.

(10) Patent No.: US 9,651,350 B2
(45) Date of Patent: May 16, 2017

(54) MEASURING ROLLER AND DEVICE FOR MEASURING A FIBER COMPOSITE

(71) Applicant: Rieter Ingolstadt GmbH, Ingolstadt (DE)

(72) Inventors: Albert Kriegler, Geisenfeld (DE); Werner Schmolke, Ingolstadt (DE); Imadettin Karalar, Ingolstadt (DE)

(73) Assignee: Rieter Ingolstadt GmbH, Ingolstadt (DE)

( * ) Notice: Subject to any disclaimer, the term of this patent is extended or adjusted under 35 U.S.C. 154(b) by 95 days.

(21) Appl. No.: 14/812,423

(22) Filed: Jul. 29, 2015

(65) Prior Publication Data

US 2016/0033252 A1    Feb. 4, 2016

(51) Int. Cl.
| | | |
|---|---|---|
| *G01B 5/06* | (2006.01) | |
| *B65H 63/06* | (2006.01) | |
| *D01H 13/32* | (2006.01) | |
| *G01N 33/36* | (2006.01) | |

(52) U.S. Cl.
CPC .............. *G01B 5/06* (2013.01); *B65H 63/06* (2013.01); *D01H 13/32* (2013.01); *G01N 33/365* (2013.01); *B65H 2701/31* (2013.01)

(58) Field of Classification Search
CPC ....................................................... G01B 5/06
USPC .................................................. 33/734–749
See application file for complete search history.

(56) References Cited

U.S. PATENT DOCUMENTS

| | | | | |
|---|---|---|---|---|
| 4,570,348 A | * | 2/1986 | Amsler | G01B 7/046 33/734 |
| 5,083,034 A | | 1/1992 | Frank et al. | |
| 5,237,754 A | | 8/1993 | Oexler | |
| 5,309,603 A | * | 5/1994 | Oexler | D01H 5/72 19/157 |
| 5,553,357 A | | 9/1996 | Kim et al. | |
| 5,796,635 A | * | 8/1998 | Dammig | G01B 7/107 19/239 |
| 6,141,883 A | * | 11/2000 | Mitchell | B65H 43/00 271/274 |
| 6,276,122 B1 | * | 8/2001 | Buchner | B65H 57/00 57/263 |
| 6,761,022 B2 | * | 7/2004 | Zipperer | D01H 13/32 57/263 |
| 2005/0278900 A1 | | 12/2005 | Dammig | |

(Continued)

FOREIGN PATENT DOCUMENTS

| | | |
|---|---|---|
| CN | 103 900 867 | 7/2014 |
| DE | 491 941 | 2/1930 |

(Continued)

OTHER PUBLICATIONS

EP Search Report, May 6, 2016.
German Patent Office Search Report, May 13, 2016.

*Primary Examiner* — Brad Bennett
(74) *Attorney, Agent, or Firm* — Dority & Manning, P.A.

(57) ABSTRACT

A measuring roller for a device for measuring a fiber composite (2), in particular on a draw frame, a carding engine or a comber, is made of a material of low thermal expansion (3) and has a surface coating (4). The measuring roller (1) features a shell surface (5) for clamping a fiber composite (6) along with a rotary axis (7). The shell surface (5) features a structure forming an air buffer, made of grooves (8), boreholes (9), and/or spherical projections (18).

12 Claims, 4 Drawing Sheets

(56) References Cited

U.S. PATENT DOCUMENTS

| | | | |
|---|---|---|---|
| 2006/0130283 A1* | 6/2006 | Strobel | B65H 54/70 19/236 |
| 2011/0137610 A1* | 6/2011 | Richter | G01B 21/08 702/170 |
| 2012/0096731 A1* | 4/2012 | Wu | G01B 5/06 33/783 |
| 2013/0067878 A1* | 3/2013 | Stephan | D01H 13/14 57/78 |
| 2014/0283497 A1* | 9/2014 | Schermer | D01H 4/10 57/406 |
| 2015/0354948 A1* | 12/2015 | Burger | G01B 11/16 73/849 |

FOREIGN PATENT DOCUMENTS

| | | |
|---|---|---|
| DE | 29 30 587 A1 | 2/1981 |
| DE | 32 19 332 A1 | 11/1983 |
| DE | 40 04 852 A1 | 9/1990 |
| DE | 195 40 340 A1 | 5/1996 |
| DE | 102 36 778 A1 | 2/2004 |
| DE | 10 2001 051 552 A1 | 1/2013 |
| JP | 2001 295 144 A | 10/2001 |
| WO | WO 91/12481 | 8/1991 |
| WO | WO 91/16595 | 10/1991 |

* cited by examiner

MEASURING ROLLER AND DEVICE FOR MEASURING A FIBER COMPOSITE

FIELD OF THE INVENTION

The present invention relates to a measuring roller for a device for measuring a fiber composite, in particular on a draw frame, a carding engine or a comber, the measuring roller is made of a material of low thermal expansion and has a surface coating. The measuring roller features a shell surface for clamping the fiber composite along with a rotary axis. Furthermore, the invention relates to a device for measuring a fiber composite with two rotatable mounted measuring rollers with shell surfaces, whereas the rotary axes of the measuring rollers are aligned parallel to each other, and the fiber composite can be passed between the shell surfaces of the measuring rollers, and with a clamping device, by means of which the gap between the measuring rollers can be changed in relation to another, and that pressure can thus be applied at the fiber composite enclosed by the measuring rollers.

BACKGROUND

A measurement system with smooth draw-off disks is currently known. The disks have the task, on the one hand, of conveying the fiber sliver and, on the other hand, of measuring the thickness of the sliver. One of the disks is movably mounted. The movable draw-off disk is pressed to the rigidly mounted disk with a defined high pressure. The deflection of the movable mounted disk is evaluated as a measurement signal. A prerequisite for a usable measurement signal is the defined high force that must act on the fiber sliver and a very high rotational accuracy of the measuring rollers. After the measuring rollers, the sliver is conveyed into a tube. For this purpose, the sliver must run into the center of the tube, since otherwise no draw-off would be possible.

A roller drafting device for a spinning machine is known from DE 10 2011 051 552 A1. Therein, a roller drafting device for drafting at least one running strand-like stacked fiber composite a work station of a spinning machine, in particular at a spinning machine or a flyer, is proposed. In doing so, a drafting field is provided for each work station, which drafting field is formed between a pair of rollers on the inlet side and a pair of rollers on the outlet side, whereas a fiber guide device for guiding the stacked fiber composite is allocated to the drafting field. In this case, the fiber guide device features a fiber guide surface, which in turn features a three-dimensional structure, in particular an orange peel structure or a honeycomb structure. Such a three-dimensional structure prevents the sticking of the stacked fiber composite at the fiber guide surface through adhesion phenomena. However, the disadvantage In this case is that the orange peel structure or the honeycomb structure is difficult to manufacture.

A device for measuring the thickness of a textile fiber composite in a drafting system is known from EP 0 478 723 B1. The device features a pair of sensing rollers, one sensing roller of which, in the axis-center distance to the other sensing roller, can be changed according to the thickness of the fiber composite. In this case, the entire fiber composite can be guided between the pair of sensing rollers, and the sensing roller that is able to be changed in the axis-center distance can be pressed against the other sensing roller. The disadvantage in doing so is that, with such sensing rollers, this may lead to adhesion phenomena between the fiber composite and the sensing rollers, which prevents a straight exit of the fiber composite from the sensing rollers. Thereby, a depositing of the fiber composite that thereafter occurs in a container provided for this purpose is difficult to control. In order to reduce the adhesion phenomena, for example, the pressure with which a sensing roller is pressed on the other sensing roller can be reduced. However, the measurement of the thickness of the fiber composite is thereby distorted. Thus, a reduction of the contact pressure of one sensing roller on the other sensing roller is rendered inapplicable.

In particular, when fine slivers are processed, the described adhesion phenomena arise. The fine sliver is entrained and deflected by the smooth roller, and thereby can no longer be conveyed into the tube. Processing is no longer possible. Previously, this effect could only be counteracted by reducing the pressing force at the movably mounted roller to the extent that a reasonably straight run was achieved. However, the reduction of the pressing force also brings about a weakening or the complete failure of the measurement signal. The monitoring of the quality parameters, including the off-limit disable function, of the exiting sliver is no longer possible.

SUMMARY OF THE INVENTION

Thus, a task of the invention is to provide a measuring roller for a device for measuring a fiber composite, which is easy to manufacture and prevents adhesion phenomena between the measuring roller and the fiber composite. Additional objects and advantages of the invention will be set forth in part in the following description, or may be obvious from the description, or may be learned through practice of the invention.

The tasks are solved by a measuring roller for a device for measuring a fiber composite and a device for measuring a fiber composite as described herein.

A measuring roller for a device for measuring a fiber composite, in particular at a draw frame, a carding engine or a comber, is proposed. Thereby, the measuring roller is manufactured from a material of low thermal expansion, in order to, if there is a warming up of the measuring roller through the friction between it and the fiber composite, reduce any distortion of the measurement.

The measuring roller also features a surface coating, which reduces the wear of the measuring roller. A suitable surface coating may comprise, for example, chromium.

Furthermore, the measuring roller features a shell surface for clamping a fiber composite along with a rotary axis.

In accordance with the invention, the shell surface of the measuring roller features a structure forming an air buffer, made of grooves, boreholes, and/or spherical projections. Through the grooves, boreholes and/or spherical elevations, the contact surface between the shell surface and the fiber composite is reduced. Such contact surface is also referred to as the active surface. In the grooves or boreholes and/or between the spherical projections, an air buffer or an air cushion is formed, and/or air can flow to the side through the grooves or boreholes and/or between the spherical projections in the direction of the fiber composite. Thereby, the air cushion is located between the shell surface and the fiber composite, thus reducing the adhesion phenomenon. By reducing the adhesion phenomenon, any entrainment and deflection of the fiber composite or even any winding of the fiber sliver in the circumferential direction around the measuring roller is reduced or entirely avoided. With a device in which the measuring roller is arranged, a sliver funnel and a rotary disk may be arranged downstream; this deposits the fiber composite in a can. Thereby, the sliver funnel and the rotary plate feature a tube, through which the fiber composite is introduced into the rotary disk. By reducing the adhesion phenomenon, the fiber composite may advantageously be introduced in a straight line and in particular in the center of the tube. Thus, the fiber composite may be deposited on a controlled basis into the can, in which the fiber composite is available for further processing.

In textile processing, rippling and fluting, etc. have generally been known with other applications for a long period of time. A normal, previously known form of rippling would distort the measurement signal to such a high degree that it would be useless. Through the type of ripple, the measuring system detects periodic defects. In addition, the high pressing force that is required damages the fiber material. Fine slivers with fine fibers, which are located in a position that is highly parallel within the fiber composite, such as those used (for example) in an air jet process, can be very easily damaged. This has the consequence of reduced yarn quality.

With the described geometries of the rippling, the following is achieved:
1. Straight run of the exiting fiber composite without reducing the pressing force
2. Transport of the sliver without damage to the fiber material
3. Usable measurement signal for the measurement of the sliver quality parameters.

Without the measures described, the processing of fine slivers (in particular), only losses in quality result.

It is advantageous if the grooves feature an opening angle from 40° to 105°, in particular from 60° to 84°. In addition or as an alternative, the gap between the grooves in the circumferential direction is between 0.25 mm and 1.25 mm, in particular between 0.56 mm and 0.85 mm. Likewise, In addition or as an alternative, the groove depth is between 0.1 mm and 1.0 mm, in particular between 0.2 mm and 0.45 mm. In addition or as an alternative, the groove width is between 0.2 mm and 1.0 mm, in particular between 0.41 mm and 0.59 mm. By changing the parameters, the size of the active surface may be varied. For example, the active surface becomes larger as the opening angle—with the same number of grooves—decreases. In this case, there is a dependence of the opening angle on the groove width. If the opening angle is smaller, the groove width is also reduced. Thus, with the same number and groove depth, the surface between the grooves, which constitutes the active surface, becomes larger. Likewise, the active surface becomes larger as the gap in the circumferential direction between the grooves becomes larger. In contrast, the air cushion can be enlarged as the groove depth is increased. An increase in the groove width also leads to an enlargement of the air cushion. In this case, the adhesion phenomenon decreases as the active surface becomes smaller and/or the air cushion becomes larger.

In addition, with the geometry of the grooves, damage to the fiber composite can be prevented. As described in the state of the art, in the measurement of the fiber composite, the measuring roller must be pressed with a defined pressure, in particular a sufficiently high pressure, against an additional measuring roller. Thereby, individual fibers of the fiber composite can be bent at the edges, such that they break off, and the quality of the fiber composite decreases. However, if the grooves feature, for example, a small width (for example, 0.2 mm), the individual fibers can bend into a groove only to a small degree. Thereby, the individual fibers are less bent, and the risk that these break off is reduced.

If, in addition, the opening angle of the grooves is larger, an edge between the groove and the shell surface is formed less thickly, such that the risk that the individual fibers will break off at the edges is lower.

It is also advantageous if the number of grooves in the circumferential direction is between 50 and 1000, in particular between 200 and 400. The circumference is, for example, between 100 and 250 mm, preferably approximately 170 mm. Thereby, the size of the active surface can be varied. Thereby, the number of grooves in the circumferential direction is dependent on the groove width, the opening angle of the grooves, the groove depth and gap between the grooves in the circumferential direction. In addition, a pitch angle also results from the number of grooves. This is calculated from the 360° of a full circle divided by the number of grooves. Thus, the pitch angle is between 0.36° and 7.2°, in particular between 0.9° and 1.8°. A pitch also results from the number of grooves. Such pitch arises from the circumference of the measuring roller divided by the number of the grooves. The pitch is between 0.1 mm and 5 mm. Thereby, a higher number of grooves leads to a decrease in the active surface, and in turn to a lower adhesion phenomenon.

In order to make available one additional parameter in order to influence the adhesion phenomenon, it is advantageous if at least a part of the grooves intersects at an angle of 0° to 90°, in particular at an angle of 16° to 75°. In this case, at least one part of the grooves is arranged axially, and the other part of the grooves features the angle to the axial grooves. Alternatively, it is also possible that both parts of the grooves run obliquely across the shell surface of the measuring roller, but herein still intersect at the angle, so that grooves running obliquely opposite are formed. Thus, the grooves are formed in such a manner that they have a connection with each other. If the angle is 0°, all of the grooves are located parallel to each other. Thereby, the grooves may be formed as longitudinal, transverse and/or oblique grooves; that is, the grooves are arranged in an axial direction, a circumferential direction or oblique to the shell surface of the measuring roller. If the grooves intersect with each other, this leads to the fact that the air cushion can be distributed between the respective grooves and can be formed so rapidly that the adhesion phenomenon is reduced.

For example, if the grooves are arranged in a circumferential direction, the risk that the individual fibers will break off can be prevented. With this arrangement of the grooves, the individual fibers are arranged parallel to the grooves, such that the individual fibers can be deposited in the grooves, whereby these are not able to bend.

An additional advantage occurs if the diameter of the boreholes at the shell surface is between 0.1 mm and 1.25 mm, in particular between 0.25 mm and 0.75 mm. Through larger boreholes, the active surface is also reduced, and the air cushion between the shell surface of the measuring roller and the fiber composite is increased, which has a positive effect on the adhesion phenomenon. However, it is not necessary that all the boreholes feature the same diameter. Since, with any alignment of round boreholes, an intermediate space is formed, it is conceivable that the smaller boreholes are arranged in such intermediate space. It is also advantageous if the boreholes are obliquely drilled on the shell surface, in particular in the side areas. This leads to a further reduction of the active surface, and thus to a reduction in the adhesion phenomenon. Moreover, smaller boreholes (for example) reduce the risk that the individual fibers in the fiber composite are bent, and thus the quality of the fiber composite is impaired.

In addition or as an alternative, it is particularly advantageous if the depth of the borehole is between 0.1 mm and 1.0 mm, in particular between 0.2 mm and 0.45 mm. Through a greater depth of the boreholes, the air cushion is also larger, which in turn leads to a reduction in the adhesion phenomenon. At a lower depth of the borehole, the individual fibers cannot be bent so far that they break off. In contrast, the individual fibers at a greater depth of the boreholes are bent "more softly" in the boreholes, such that the risk that the fibers break off at the edge between the borehole and the shell surface is reduced.

It is also advantageous if the number of boreholes at the shell surface is between 1,000 and 25,000, in particular between 5,000 and 15,000. Through a higher number of boreholes, the size of the active surface decreases, which also reduces the adhesion phenomenon.

Another advantage also arises if the spherical projections feature a radius of between 0.1 µm and 10 µm, in particular between 0.6 µm and 4 µm. Here, the air cushion is located between the projections. Similar to the boreholes, it is also the case with the spherical projections that, for any alignment of spherical projections, intermediate spaces are formed. In such intermediate spaces, smaller spherical projections may, of course, also be arranged. Therefore, it is generally conceivable that the spherical projections on the shell surface have different sizes, and/or are distributed randomly or arbitrarily across the shell surface. In this case, the air cushion is enlarged if, for example, one or more smaller spherical projections are arranged between larger spherical projections. This reduces the adhesion phenomenon.

In addition, such spherical projections with a radius in such areas are advantageous, since the individual fibers of the fiber composite feature a cross-section that is larger than that of the projections. Thus, an air buffer can be formed that cannot be affected, or can barely be affected, by the individual fibers, since the fibers cannot penetrate the intermediate spaces between the projections. Likewise, the individual fibers are not damaged by the projections, since their spherical shape does not feature any sharp edges. The fibers are also not bent by the projections that are smaller relative to the fibers, such that the fibers cannot break off.

Another advantage to be mentioned arises if the shell surface features a roughness value, formed by the spherical projections, between 0.5 and 80, in particular between 10 and 60. Thereby, the roughness value is indicated by an average surface roughness. Furthermore, there is a relationship between the roughness value and the size of the spherical projections. Generally, the roughness value also increases with larger spherical projections.

A vanishing of the roughness is equivalent to a smooth shell surface, which leads to the undesired adhesion phenomenon. An increase in roughness then leads to an enlargement of the air cushion, which in turn leads to a decreasing adhesion phenomenon.

In addition, it is also advantageous if the material of a low thermal expansion is an Invar material with a thermal expansion coefficient of 0.55 to 1.7 10e-6 1/K. Given the friction between the fiber composite and the measuring roller and given the machine itself, heat is generated, which in turn warms up the measuring roller. This leads to an expansion of the measuring roller, whereby the measurement of the fiber composite is distorted. However, because of the Invar material with a low thermal expansion coefficient, this effect remains so low that it falls below a tolerance of the measurement. Thereby, the most common Invar material is an alloy of 64% iron and 36% nickel. However, other materials that have a low thermal expansion coefficient are, of course, also conceivable.

An additional advantage arises if the shell surface is coated with a surface coating such as (for example) a chromium layer. This surface coating may also feature a roughness, by which the adhesion phenomenon is likewise reduced. Given the surface coating, wear during the use of the measuring roller is reduced, which has the effect of reducing costs and extends the maintenance intervals.

It is particularly advantageous if the ratio of the size of the active surface to the size of the shell surface is between 15% and 85%, in particular between 26.5% and 62.4%. Thereby, in a known manner, the size of the shell surface is calculated by multiplying the circumference and the width of the measuring roller. In this case, the width of the measuring roller is between 5 mm and 30 mm, in particular approximately 15 mm. The active surface is thereby calculated, likewise in a known manner, by multiplying the width of the measuring roller, the gap of the grooves from one another in a circumferential direction and their number. The greater the ratio, the greater the proportion of the active surface. With a smaller ratio, the proportion of the active surface is smaller, which leads to a larger air cushion. Thereby, a larger air cushion in turn leads to a lower adhesion phenomenon.

A device for measuring a fiber composite, with two rotatable mounted measuring rollers with shell surfaces, is also proposed, whereas the rotary axes of the measuring rollers are aligned parallel to each other, and the fiber composite can be passed between the shell surfaces of the measuring rollers.

Furthermore, the device for measuring a fiber composite includes a clamping device, by means of which the gap between the measuring rollers can be changed in relation to another, and that pressure can thus be applied at the fiber composite enclosed by the measuring rollers. For example, one measuring roller is arranged firmly in the clamping device, and the other measuring roller is arranged in a manner that is movable in respect of the fixed measuring roller. By means of the clamping device, the movable measuring roller is pressed against the stationary measuring roller at a constant pressure, whereas the fiber composite can be passed between such two measuring rollers. Upon a change to the thickness of the fiber composite, the gap between the two measuring rollers likewise changes. By means of suitable tools, such as a sensor, the gap between the two measuring rollers can be measured; this corresponds to the thickness of the fiber composite. In doing so, the thickness of the fiber composite can be drawn upon as an indicator of the quality of the fiber composite, or can be used for the purpose of an adjustment to the draw frame, the carding engine or the comber.

In addition, the two measuring rollers can also be used as draw-off rollers. By means of the draw-off rollers, the fiber composite can be conveyed through a draw frame, a carding engine and/or a comber. In this case, the draw-off rollers draw the fiber composite through the draw frame, carding engine or comber. For example, the addition to the device for measuring the fiber composite, a rotary disk and a can next to it can be arranged, whereas the fiber composite is led to the can through the rotary disk. The fiber composite is deposited in the can. Thereby, the rotary disk may comprise a tube into which the fiber composite is introduced into the rotary disk. By means of the structure of the measuring rollers forming the air buffer, an adhesion phenomenon can be prevented in accordance with the foregoing description. The adhesion phenomenon can lead to the fact, for example, that the fiber composite remains adhered to the measuring rollers, and is wrapped at least partially around the measuring rollers. In particular, the wrapping around prevents the fiber composite from entering the tube of the rotary disk in a straight line. In a particularly adverse scenario, the adhesion phenomena can wrap and deflect the fiber composite around the measuring rollers to the extent that the fiber composite runs past the tube. Thus, a controlled depositing of the fiber composite in the can is prevented.

Through the prevention of the adhesion phenomenon by means of the grooves, boreholes and/or spherical elevations, the running in of the fiber composite in a straight line into the tube of the rotary disk is provided.

At least one of the measuring rollers is formed in accordance with the previous description, whereas the specified characteristics may be present individually or in any combination.

In the event that both measuring rollers are provided with such grooves, boreholes and/or spherical projections, it is particularly advantageous if, in operation of the device, each of the peaks (or troughs) of the two measuring rollers are located opposite to each other. That is, similar to a gear wheel, a tooth-to-tooth position arises. In contrast to the position of peak on trough, this does not lead to an impression of the fiber composite through the peaks into the troughs, which results in a tolerance and/or distortion when measuring. Of course, the same is also true for the boreholes or the spherical projections.

BRIEF DESCRIPTION OF THE DRAWINGS

Additional advantages of the invention are described in the following embodiments. The following is shown.

DETAILED DESCRIPTION

Figure 1:
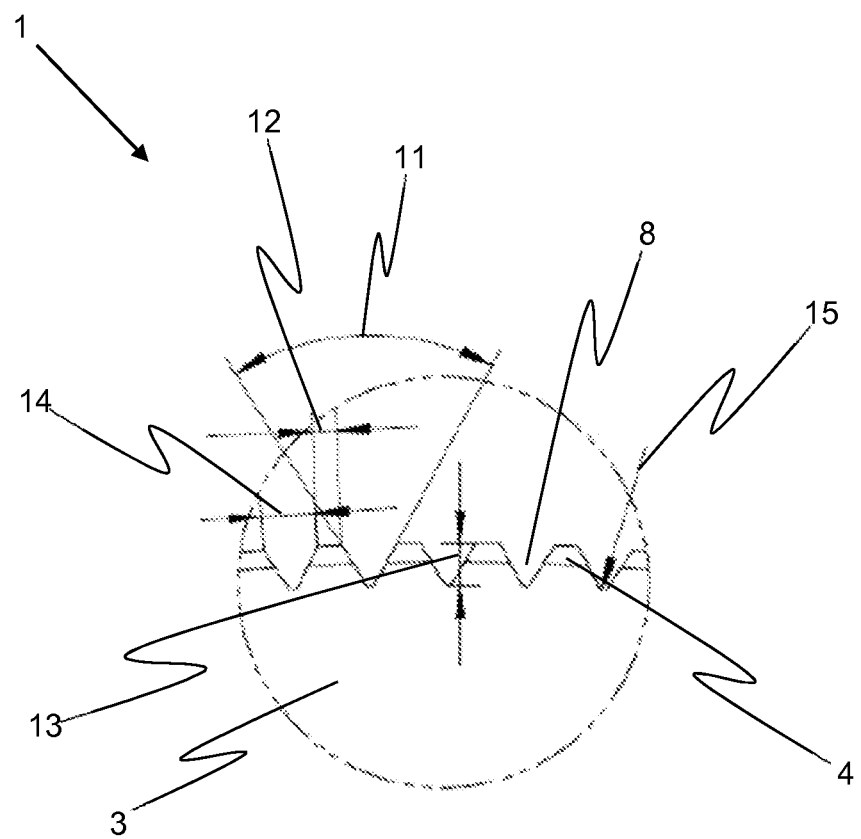
FIG. 1 Cut-out of a cross-section of a measuring roll.

Reference will now be made to embodiments of the invention, one or more examples of which are shown in the drawings. Each embodiment is provided by way of explanation of the invention, and not as a limitation of the invention. For example features illustrated or described as part of one embodiment can be combined with another embodiment to yield still another embodiment. It is intended that the present invention include these and other modifications and variations to the embodiments described herein.

FIG. 1 shows a cut-out of a cross-section of a measuring roller 1. Here the measuring roller 1 consists of a material of low thermal expansion 3. In addition, the shell surface 5 of the measuring roller 1 is coated with a surface coating 4. Grooves 8 are formed in the shell surface 5. However, in addition or as an alternative to the grooves 8, boreholes 9 (as described in FIG. 3) and/or spherical projections 18 (as described in FIG. 4) may also be formed.

Thereby, the surface coating 4 only partially covers the peak between the two grooves 8. Thus, only the active surface, which is in contact with a fiber composite 6 (FIG. 5), is coated. However, it is also conceivable that the grooves 8 are completely coated with the surface coating 4.

The grooves 8 also feature an opening angle 11. Each of the two adjacent grooves 8 have a gap in the circumferential direction 12. The grooves 8 likewise have a groove depth 13 and a groove width 14. In this case, the grooves 8 feature, in their trough, a radius 15 typical for finishing by means of, for example, milling.

Figure 2:
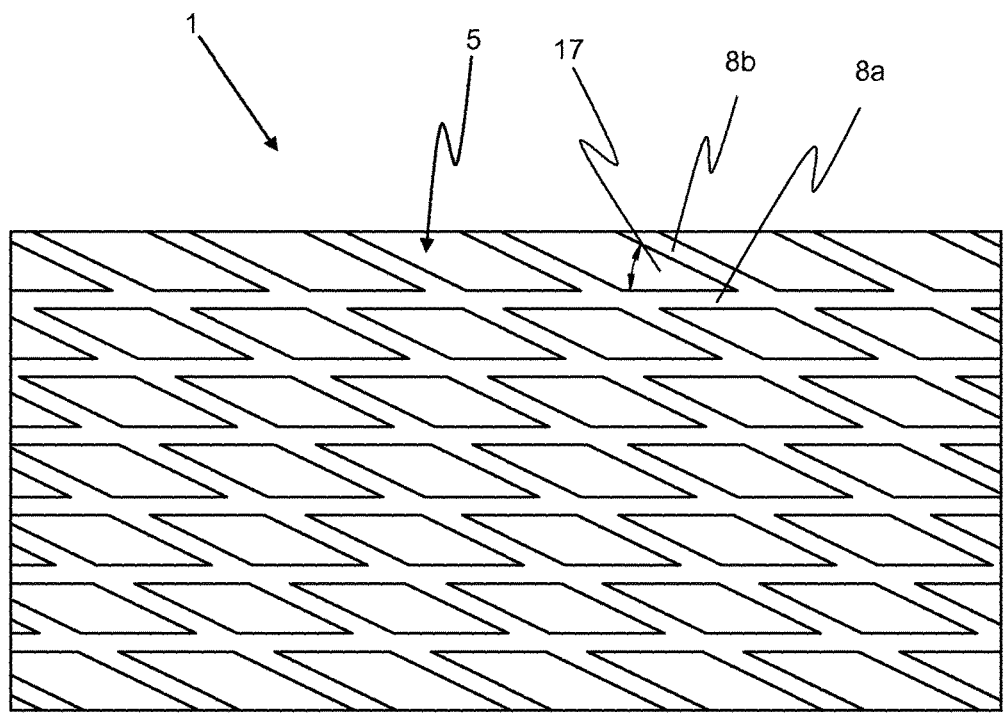
FIG. 2 Cut-out of a shell surface of a measuring roller with intersecting grooves, FIG. 3 Cut-out of a shell surface of a measuring roller with boreholes, FIG. 4 Cut-out of a cross-section of a measuring roller with spherical projections, and FIG. 5 Device for measuring a fiber composite with two measuring rollers.

FIG. 2 shows a cut-out of the shell surface 5 of the measuring roller 1 with intersecting grooves 8. In this case, a first part of the groove 8a is aligned only in an axial direction. A second part of the grooves 8b intersects the first part of the grooves 8a at an angle 17. Since the part of the grooves 8a intersects with the part of the grooves 8b at the angle 17, a connection between the respective grooves 8a and 8b is formed. An air cushion may then arrive through one groove 8b from one of the grooves 8a into an adjacent groove 8a.

It is not mandatory that a part of the grooves 8 is axially aligned. It is also possible that both parts of the grooves 8a and 8b run obliquely (but still intersecting at the angle 17) to the shell surface 5 of the measuring roller 1. This leads to two opposing parts of the grooves 8a and 8b.

Figure 3:
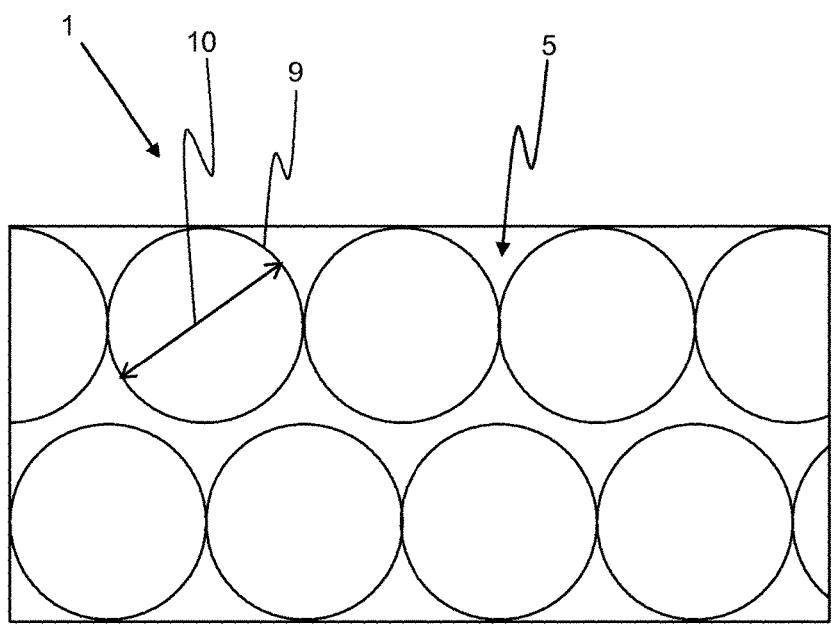

FIG. 3 shows a cut-out of the shell surface 5 of the measuring roller 1 with boreholes 9. Here, the boreholes 9 feature a diameter 10. The uniform alignment of the boreholes 9 is one example of this. It would also be conceivable that the boreholes have different diameters 10. It is also conceivable that the boreholes 9 are distributed in a different arrangement or randomly across the shell surface 5.

Figure 4:
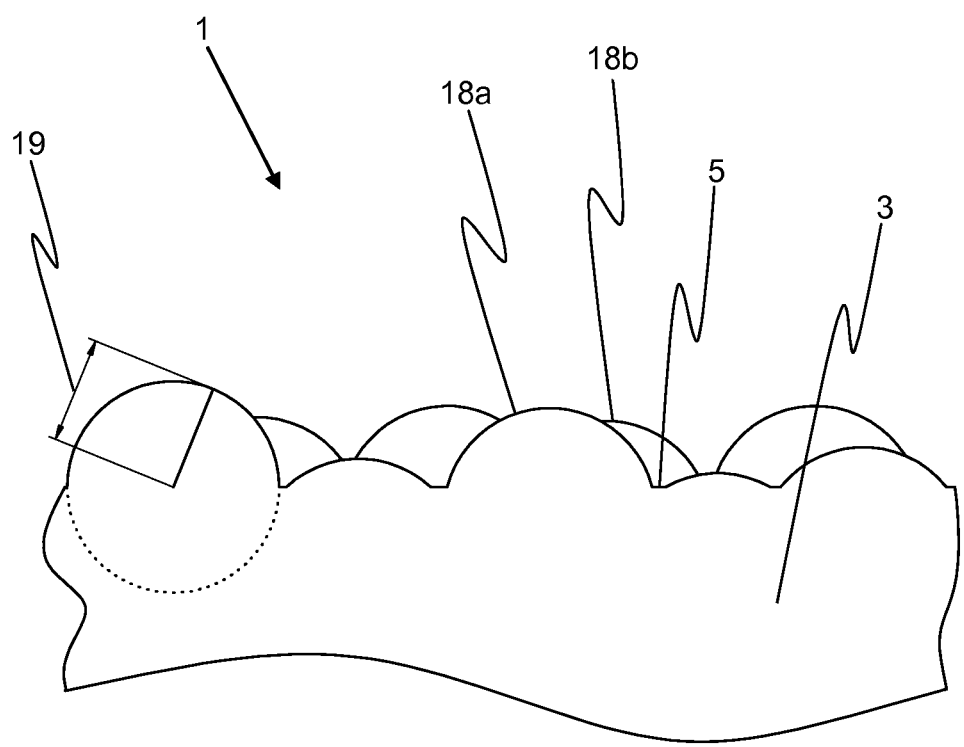

FIG. 4 shows a cut-out of a cross-section of a measuring roller 1 with spherical projections 18. The measuring roller 1 is here formed from a material of low thermal expansion 3. The spherical projections 18a and 18b are arranged on the shell surface 5, whereas, based on the overview, only these two are provided with reference signs. In this figure, the spherical projection 18a is located in the foreground. There is a smaller spherical projection 18b behind it. As can be seen, the spherical projections 18 are not arranged in any pattern; that is, the sizes of the spherical projections, the alignment and the gaps between them are largely arbitrary. However, a regular alignment, by which all spherical projections have the same size and are evenly arranged, is possible. The spherical projections feature a radius 19, whereas, for ease of understanding, the full radius of the spherical projection is indicated by the dotted line (and the full line).

Figure 5:
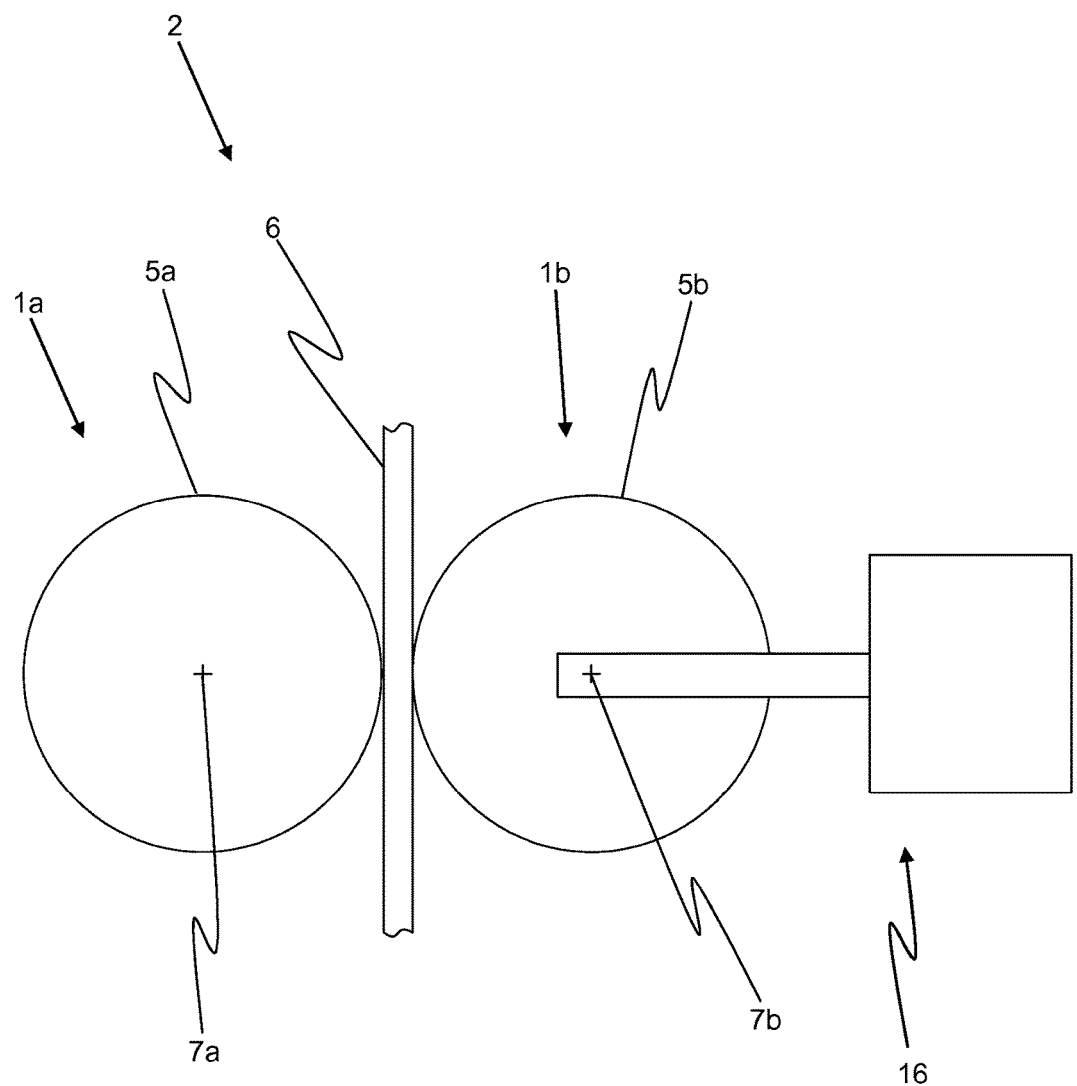

FIG. 5 shows a device for measuring a fiber composite 2 with two measuring rollers 1a and 1b. The measuring rollers 1a and 1b include the respective shell surfaces 5a and 5b. A fiber composite 6 can be passed between the shell surfaces 5a and 5b. The measuring rollers 5a and 5b are rotatable mounted around the respective rotary axes 7a and 7b. A pressing device 16 exerts pressure on the measuring roller 5b, such that the gap between the measuring rollers 5a and 5b changes depending on the thickness of the fiber composite 6.

The gap between the two measuring rollers 5a and 5b is incorporated by an arrangement that is not shown here. This gap then corresponds to the thickness of the fiber composite 6.

The invention is not limited to the illustrated and described embodiments. Variations within the framework of the patent claims, such as a combination of features, are also possible, even if such are presented and described in different embodiments.

LIST OF REFERENCE SIGNS

1. Measuring roller
2. Device for measuring a fiber composite

3. Material of low thermal expansion
4. Surface coating
5. Shell surface
6. Fiber composite
7. Rotary axis
8. Groove
9. Borehole
10. Diameter of the borehole
11. Opening angle
12. Gap in the circumferential direction
13. Groove depth
14. Groove width
15. Radius
16. Clamping device
17. Angle
18. Spherical projection
19. Radius

The invention claimed is:

1. A measuring roller for a device (2) for measuring a fiber composite (6) on a draw frame, a carding engine, or a comber, the measuring roller comprising:
 a rotary axis (7);
 the measuring roller formed of a material having a thermal expansion characteristic to resist expansion from warming of the measuring roller through friction between the measuring roller and the fiber composite;
 a shell surface (5) for clamping the fiber composite (6);
 a surface coating (4) over the shell surface (5); and
 wherein the shell surface (5) comprises any one or combination of grooves, boreholes, or projections that form an air buffer between the shell surface and the fiber composite.

2. The measuring roller according to claim 1, wherein the shell surface comprises grooves (8) with an opening angle (11) from 40° to 105°, and a circumferential gap (12) between adjacent grooves from 0.25 mm to 1.25 mm, the grooves having a groove depth (13) from 0.1 mm to 1.0 mm and a groove width (14) from 0.2 mm to 1.0 mm.

3. The measuring roller according to claim 2, wherein a number of the grooves (8) in the circumferential direction is between 50 and 1000.

4. The measuring roller according to claim 2, wherein the grooves are parallel.

5. The measuring roller according to claim 2, wherein the grooves are arranged in an intersecting pattern such that a first portion of the grooves intersect a second portion of the grooves at an angle (17) of 16° to 75°.

6. The measuring roller according to claim 1, wherein the shell surface comprises boreholes (10) having a diameter between 0.1 mm and 1.25 mm and a depth between 0.1 mm and 1.0 mm.

7. The measuring roller according to claim 6, wherein a number of the boreholes (9) at the shell surface (5) is between 1,000 and 25,000.

8. The measuring roller according to claim 1, wherein the shell surface comprises spherical projections (18) with a radius (19) of between 0.1 μm and 10 μm.

9. The measuring roller according to claim 8, wherein the shell surface has a roughness value, formed by the spherical projections (18), between 0.5 and 80.

10. The measuring roller according to claim 1, wherein the material is Invar material with a thermal expansion coefficient of 0.55 10e-6 1/K to 1.7 10e-6 1/K.

11. The measuring roller according to claim 1, wherein a ratio of size of an active surface of the shell surface (5) that contacts the fiber composite to a total size of the shell surface (5) is between 15% and 85%.

12. A device for measuring a fiber composite, comprising:
 opposed rotatable mounted measuring rollers (1a, 1b) with respective shell surfaces (5a, 5b), whereas rotary axes (7a, 7b) of the measuring rollers (1a, 1b) are aligned parallel to each other, and the fiber composite (6) is passed through a gap between the shell surfaces (5a, 5b) of the measuring rollers (1a, 1b);
 a clamping device (16) configured with one of the measuring rollers to change the gap between the measuring rollers (1a, 1b) and apply pressure via the measuring roller to the fiber composite passing through the gap; and
 wherein at least one of the measuring rolls (1a, 1b) is in accordance with the measuring roller of claim 1.

* * * * *